US006480562B2

(12) United States Patent
Jiang et al.

(10) Patent No.: US 6,480,562 B2
(45) Date of Patent: Nov. 12, 2002

(54) APPARATUS AND METHOD OF CONVERTING ELECTROMAGNETIC ENERGY DIRECTLY TO ELECTRONS FOR COMPUTED TOMOGRAPHY IMAGING

(75) Inventors: Haochuan Jiang, Brookfield, WI (US); David M. Hoffman, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 27 days.

(21) Appl. No.: 09/681,047

(22) Filed: Dec. 5, 2000

(65) Prior Publication Data

US 2002/0067795 A1 Jun. 6, 2002

(51) Int. Cl.[7] .................................................. A61B 6/00
(52) U.S. Cl. ............................ 378/19; 378/91; 378/98.8
(58) Field of Search ................................ 378/4, 19, 91, 378/98.8; 117/1, 4

(56) References Cited

U.S. PATENT DOCUMENTS

| 4,855,589 A | * | 8/1989 | Enck et al. | ........... 250/214 VT |
| 5,635,706 A | * | 6/1997 | She et al. | ............. 250/214 VT |
| 6,272,207 B1 | * | 8/2001 | Tang | ........................... 378/149 |

OTHER PUBLICATIONS

Christensen's Physics of Diagnostic Radiology, Curry, Dowdey and Murray (eds), Lippincott, Williams and Wilkins, 4th Edition, pp. 289–323.*
Beutel, J; Knudel, H.L.; Van Metter, R.L.: Handbook of Medical Imaging, vol. 1. Physics and Psychophysics. ©2000 The Society of Photo–Optical Instrumentation Engineers.
Inorganic Products (bicorn.com/CSI/docs/science/how_12/xray_scintillators).
Imagine the Universe (Scintillator X–ray Detectors (imagine.gsfc.nasa.gov).
Properties of Scintillators (oden.nuc.ucla.edu/s200b/lecture3/scint1).
Scintillators (oden.nuc.ucla.edu/rs200b/lecture3/scint2).
Organic Scintillators (oden.nuc.ucla.edu/rs200b/lecture3/scint3).
Organic Scintillators (oden.nuc.ucla.edu/s200b/lecture3/scint4).
Inorganic Scintillators (oden.nuc.ucla.edu/rs200b/lecture3/scint5).
Inorganic Scintillators (oden.nuc.ucla.edu/rs200b/lecture3/scint6).
Inorganic Scintillators (oden.nuc.ucla.edu/rs200b/lecuture3/scint7).
Properties of Scintillators (oden.nuc.ucla.edu/rs200b/lecture3/scint8).

(List continued on next page.)

*Primary Examiner*—David P. Porta
*Assistant Examiner*—Therese Barber
(74) *Attorney, Agent, or Firm*—Timothy J. Ziolkowski; Michael A. Della Penna; Carl B. Horton

(57) ABSTRACT

The present invention provides a detector for a multi-slice CT system. The detector includes a scintillator for receiving and converting high frequency electromagnetic energy directly to electrons. The detector is further configured to directly conduct the electrons. The detector comprises a compound formed of scintillator bulk and a conducting material capable of converting high frequency energy to electrons as well as conduct electrons. The CT system also provides for a gantry having an output for projecting high frequency electromagnetic energy toward the detector and a data acquisition system for receiving electrons directly from the detector. A method to provide imaging electrons to a CT system is also provided.

26 Claims, 4 Drawing Sheets

OTHER PUBLICATIONS

Properties of Scintillators (oden.nuc.ucla.edu/rs200b/lecture3/scint9).
Properties of Scintillators (oden.nuc.ucla.edu/rs200b/lecture3/scint10).
Properties of Scintillators (oden.nuc.ucla.edu/rs200b/lecture3/scint11).
Properties of Scintillators (oden.nuc.ucla.edu/rs200b/lecture3/scint12).
Properties of Scintillators (oden.nuc.ucla.edu/rs200b/lecture3/scint13).
Properties of Scintillators (oden.nuc.ucla.edu/rs200b/lecture3/scint14).
Crystran Caesium Iodide (CsI) Data Sheet (crystran.co.uk./csidata).
Crismatec Photodiode Scintillation Detectors (crismatec.com/scintillation/ph).

* cited by examiner

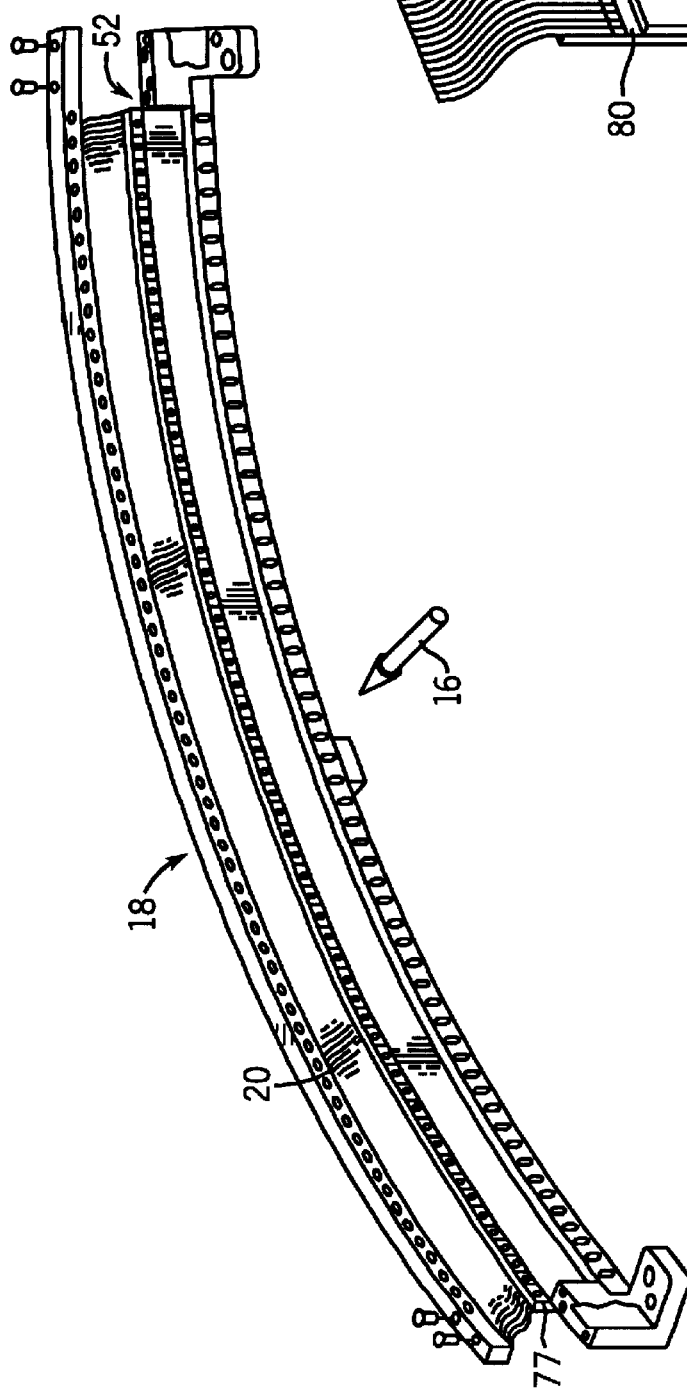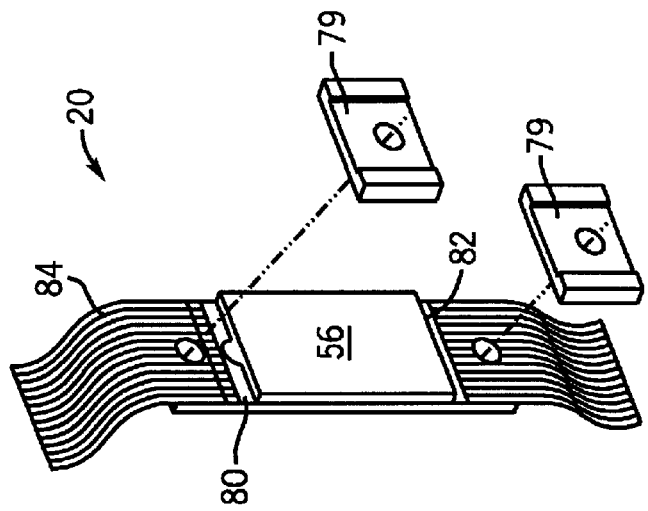

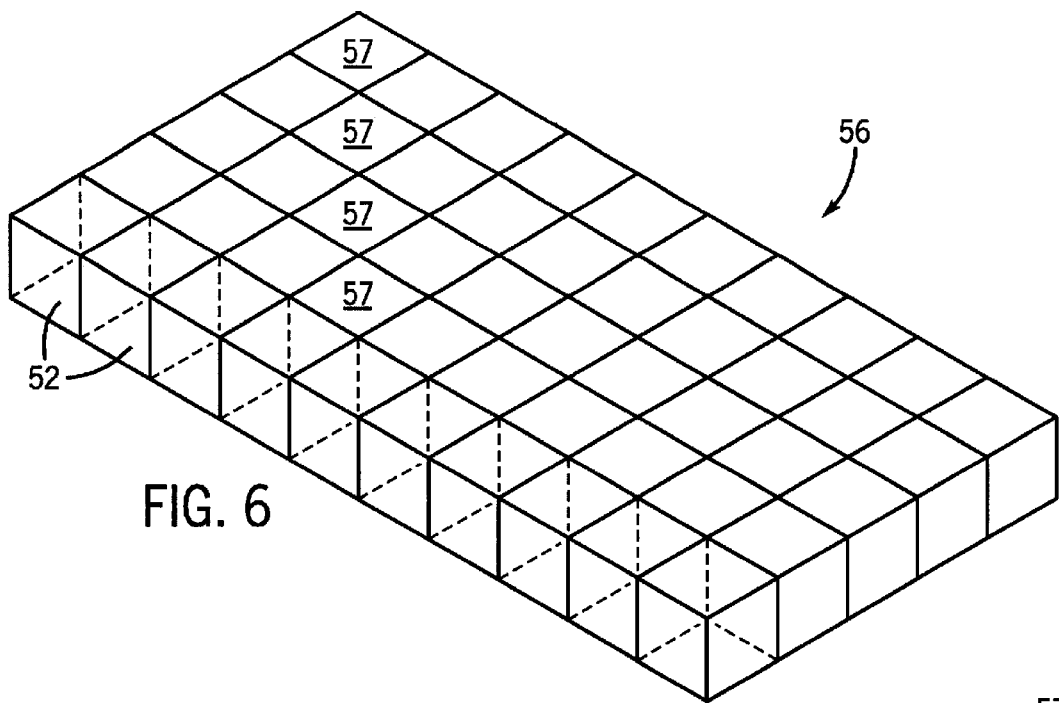
FIG. 6
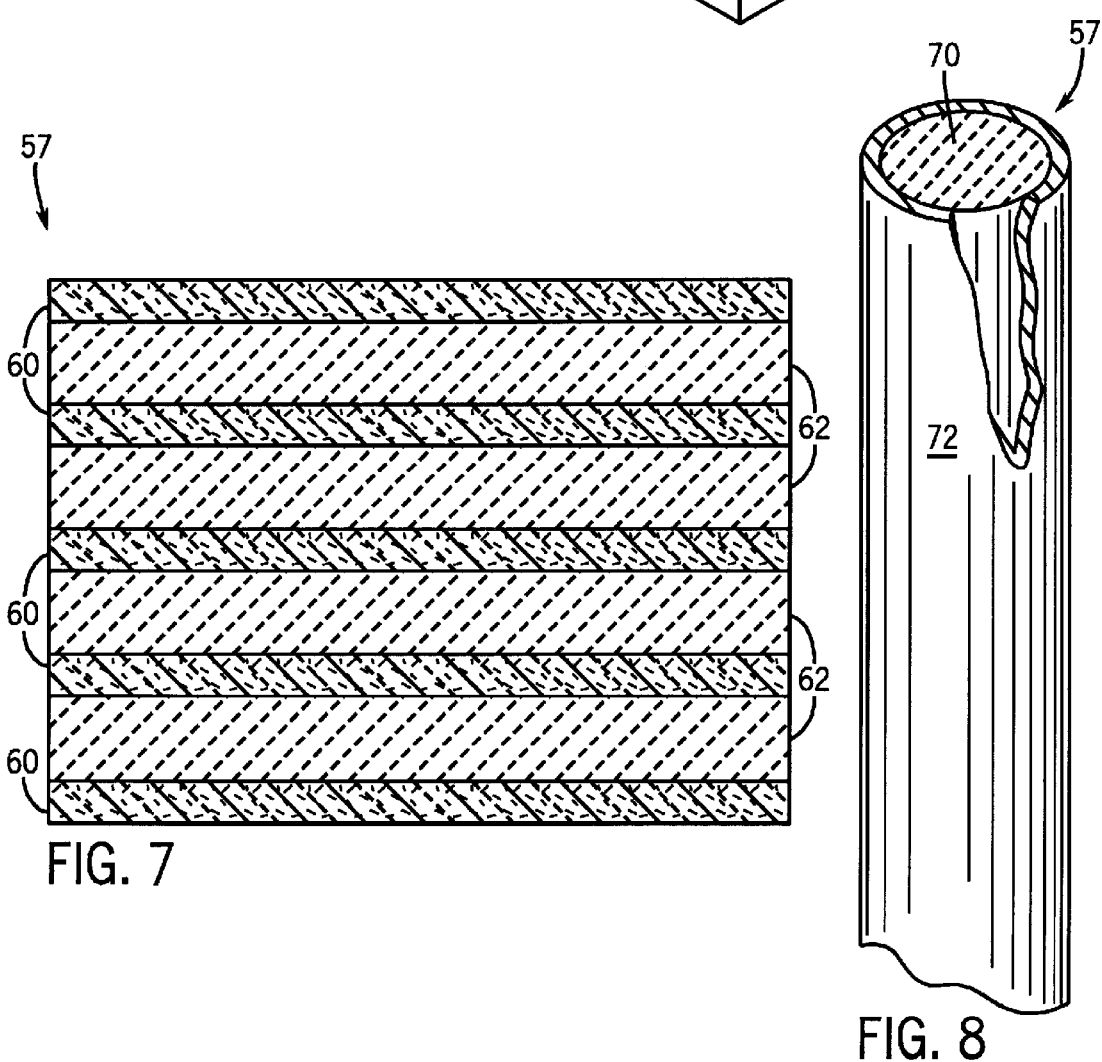
FIG. 7
FIG. 8

APPARATUS AND METHOD OF CONVERTING ELECTROMAGNETIC ENERGY DIRECTLY TO ELECTRONS FOR COMPUTED TOMOGRAPHY IMAGING

BACKGROUND OF INVENTION

The present invention relates generally to the detection and conversion of high frequency electromagnetic energy to electrical signals and, more particularly, to an apparatus and method of directly converting x-rays to electrons for use with computed tomography systems.

Typically, in computed tomography (CT) imaging systems, an x-ray source emits a fan-shaped beam toward an object, such as a patient. The beam, after being attenuated by the object, impinges upon an array of radiation detectors. The intensity of the attenuated beam radiation received at the detector array is typically dependent upon the attenuation of the x-ray beam by the object. Each detector element of the detector array produces a separate electrical signal indicative of the attenuated beam received by each detector element. The electrical signals are transmitted to a data processing system for analysis which ultimately results in the formation of an image.

Generally, the x-ray source and the detector array are rotated about the gantry within an imaging plane and around the object. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to a data processing system. Typically, the photodiode array is formed on a silicon chip, therefore, complicated and extremely expensive fabrication techniques are required. As a result, the CT imaging system may be unduly complicated and cost prohibitive.

Furthermore, typical scintillators for CT imaging systems have a limited thickness. Generally, the scintillator thickness must be sufficient to stop penetration of the high frequency energy through the scintillator to the remainder of the detector components. However, for each photodiode to efficiently detect emitting light energy, the scintillator thickness should be thin. As a result, design of typical scintillators requires a scintillator of reduced stopping power which, over time, reduces the overall performance and functional life span of the CT system.

It would therefore be desirable to have a scintillator with increased thickness and stopping power capable of converting high frequency electromagnetic energy directly to electrons and directly transmitting the electrons to a data processing system for CT image construction.

SUMMARY OF INVENTION

The present invention provides a detector for a CT system that overcomes the aforementioned drawbacks. The detector includes a scintillator for receiving and converting high frequency electromagnetic energy directly to electrons. The detector is further configured to directly conduct the electrons. The detector comprises a compound formed of scintillator bulk and conducting material capable of converting high frequency energy to electrons as well as conducting electrons. The CT system also provides for a gantry having an output for projecting high frequency electromagnetic energy toward the detector and a data processing system for receiving electrons directly from the detector.

In accordance with one aspect of the invention, a detector for a computed tomography system is provided. The detector includes a scintillator array having a plurality of scintillators therein capable of receiving high frequency electromagnetic energy, converting the electromagnetic energy directly to electrons, and transmitting those electrons directly to a data processing system.

In accordance with another aspect of the invention, a composite for an image detection CT system includes both a bulk to directly convert high frequency electromagnetic energy to electrons and a conducting material. The conducting material is also capable of converting the high frequency electromagnetic energy to electrons and is further capable of conducting the electrons to a plurality of electrical interconnects.

The invention also includes a method to provide imaging electrons to a data acquisition system of a CT system. The method includes directing high frequency electromagnetic energy towards a scintillator housing having therein a scintillator. The method further includes providing a scintillator capable of converting high frequency electromagnetic energy directly to electrons and then conducting those electrons to a data acquisition system for CT image construction.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

FIG. 6 is a perspective view of one embodiment of the present invention.

FIG. 7 is a cross-sectional view of another embodiment of the present invention.

FIG. 8 is a cut-away perspective view of a portion of another embodiment of the present invention.

DETAILED DESCRIPTION

The operating environment of the present invention is described with respect to a four-slice computed tomography (CT) system. However, it will be appreciated by those of ordinary skill in the art that the present invention is equally applicable for use with single-slice or other multi-slice configurations. Moreover, the present invention will be described with respect to the detection and conversion of x-rays. However, one of ordinary skill in the art will further appreciate, that the present invention is equally applicable for the detection and conversion of other high frequency electromagnetic energy.

Figure 1:
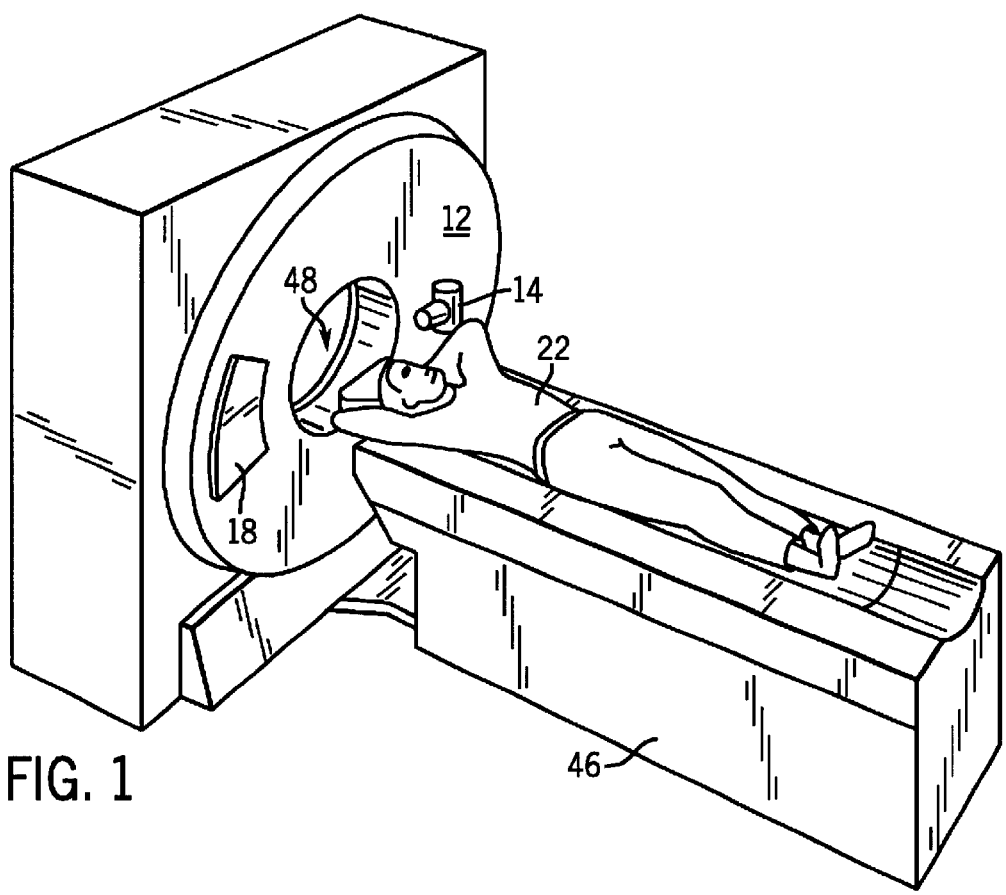
FIG. 1 is a pictorial view of a CT imaging system.
Figure 2:
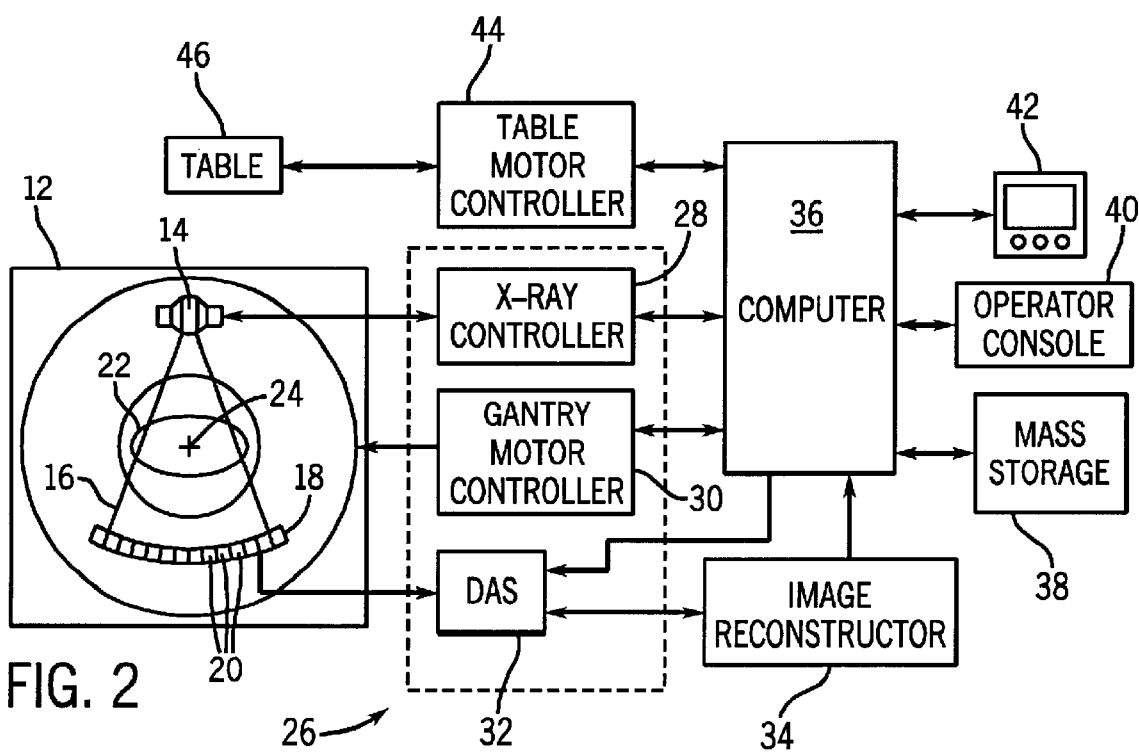
FIG. 2 is a block schematic diagram of the system illustrated in FIG. 1.

Referring to FIGS. 1 and 2, a computed tomography (CT) imaging system 10 is shown as including a gantry 12 representative of a third generation CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective scintillators and a number of output leads electrically connected to DAS 32 via a flexible electrical interface 84. Particularly, about ½ of scintillator outputs are electrically connected to switch 80 with the other ½ of scintillator outputs electrically connected to switch 82. Each detector 20 is secured to a detector frame 77, FIG. 3, by mounting brackets 79.

Switch arrays 80 and 82 further include a decoder (not shown) that control enables, disables, or combines scintillator outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the scintillator array 52 are activated, resulting in 16 simultaneous slices of data for processing by DAS 32. Of course, many other slice combinations are possible. For example, decoder may also select from other slice modes, including one, two, and four-slice modes.

Figure 5:
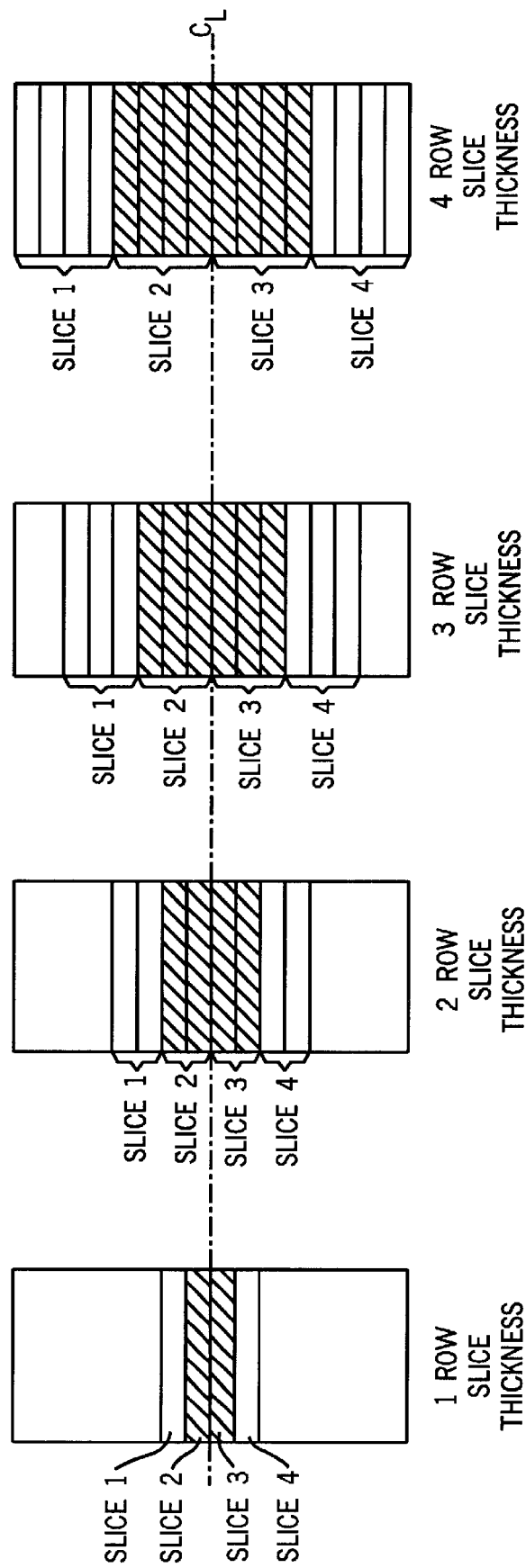
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of scintillator array 56. Depending upon the specific configuration of switch arrays 80 and 82, various combinations of scintillators 57 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

To facilitate the construction of a CT image by converting x-rays directly to electrons and transmitting those electrons directly to a signal run, a composite for a scintillator 57 of the scintillator array 56 is disclosed. Each scintillator 57 of the scintillator array 56 is formed of a bulk selected from a group consisting of undoped cesium iodide (CsI), cesium bromide (CsBr), lead oxide (PbO), and a photoemissive conducting or semiconducting compound. In one preferred embodiment, the conducting compound comprises potassium cesium antimide (KCsSb). The conducting material may also comprise compounds of other heavy materials, such as, cesium (II) antimide ($Cs_3Sb$), rubidium cesium antimide (RbCsSb), sodium cesium antimide (NaCsSb), and lithium cesium antimide (LiCsSb).

Alternatively, the photoemissive semiconducting material comprises cadmium telluride (CdTe), but other photoemissive semiconducting compounds, such as gallium arsenide (GaAs), indium arsenide (InAs), gallium arsenic cesium (GaAs—Cs), and lead telluride (PbTe), are applicable with the present invention.

Now referring to FIG. 6, and in a preferred embodiment, each scintillator 57 of scintillator array 56 has a single phase composite structure comprising 40–80% undoped CsI and 20–60% CdTe. The scintillator 57 having a single phase composite structure is formed by mixing the undoped CsI and the CdTe, which in a preferred embodiment, are each powder. After mixing, the mixture is isopressed or compacted under extremely high pressure, typically, several thousand psi. Isopressing or compacting the mixture is necessary to eliminate any porosity of the mixture. The isopressed or compacted mixture then undergoes heat-treating. The heat-treating, or sintering, melts the mixture to eliminate any remaining pores of the mixture as well as permit molding of the composite to one of a number of different forms, including the single phase form shown in FIG. 6.

An additional form for each scintillator 57 of the scintillator array 56 is shown in a cross-sectional view in FIG. 7. In this embodiment, the scintillator 57 has a multi-phase composite structure illustrated by several layers of conducting material 60 interspersed between alternating bulk layers 62 of undoped Cs, CsBr, or PbO 62. In a preferred embodiment, the width of each conducting layer 60 is approximately 5–15 micrometers and the width of each bulk layer 62 is approximately 50–100 micrometers. However, one of ordinary skill in the art will appreciate that the widths of each layer 60 and 62 are not limited to the dimensions referenced above. The overall width of the scintillator 57, however, must be such that the x-rays entering the scintillator 57 are absorbed and not discharged.

The present invention, regardless of embodiment, allows for a scintillator of arbitrary thickness provided a minimum of x-rays are stopped from exiting the scintillator. This permits some flexibility in scintillator design, such as a fiber bundled scintillator array configuration, shown in FIG. 8. In a fiber bundle configuration each scintillator 57 of the scintillator array 56 has a cylindrical configuration. To facilitate this configuration, the undoped CsI is compacted and heat-treated as a solid cylindrical tube 70. To permit the efficient conducting of electrons produced by the undoped CsI 62, a thin layer 72 of CdTe is wrapped around the solid of undoped CsI 62. When the x-rays are projected toward the scintillator 57 and converted to electrons by the undoped CsI, the electrons are then transmitted for processing by the thin conducting layer 72 wrapped therearound. To prevent conductance of electrons between separate scintillators, each scintillator 57 has a thin insulating sheath (not shown) wrapped therearound.

The present invention, therefore, provides imaging electrons for a data acquisition system for a computed tomography system absent the need for a photodiode array having a plurality of photodiodes. Accordingly, a method of providing imaging electrons for a CT system is disclosed. The method includes providing a scintillator capable of converting x-rays directly to electrons and further capable of conducting those electrons to a data acquisition system for processing. The method includes compacting and sintering a mixture of undoped CsI and CdTe, in a preferred embodiment, to form the disclosed scintillator 57. The method also includes configuring the composite in a pixelating, columnating, or layered form. Regardless of the form, x-rays projected toward the scintillator 57 are directly converted to electrons and transmitted to the data acquisition system.

The present invention has been described in terms of the preferred embodiment, and it is recognized that equivalents, alternatives, and modifications, aside from those expressly stated, are possible and within the scope of the appending claims.

What is claimed is:

1. An apparatus to detect and convert high frequency electromagnetic energy to electrons, comprising:
   a plurality of electrical interconnects forming a signal run; and
   a scintillator array having a plurality of scintillators therein, each scintillator comprising a single phase of composite material configured to convert high frequency electromagnetic energy directly to electrons and to conduct those electrons to the signal run.

2. The apparatus of claim 1 incorporated into a computed tomography system and further including an interface configured to transmit signals from the signal run to a data processing system configured to reconstruct an image based on the signals and visually display the image, and wherein each scintillator is configured as an electrical conductor.

3. The apparatus of claim 1 wherein the single phase composite material is formed of a bulk selected from a group of materials comprising undoped CsI, CsBr, and PbO, and a photoemissive conducting compound.

4. The apparatus of claim 3 wherein the photoemissive conducting compound is capable of converting the high frequency electromagnetic energy to electrons.

5. The apparatus of claim 4 wherein the photoemissive conducting compound is selected from a group consisting of KCsSb, $Cs_3Sb$, RbCsSb, NaCsSb, and LiCsSb.

6. The apparatus of claim 3 wherein the conducting compound is a photoemissive semiconductor compound selected from a group consisting of CdTe, GaAs, InAs, GaAs—Cs, and PbTe.

7. The apparatus of claim 1 constructed without a photodiode array and photodiodes therein.

8. The apparatus of claim 1 wherein the scintillator array is pixelated and includes an inlet surface, an outlet surface, and a number of sidewalls connecting the inlet surface to the outlet surface.

9. The apparatus of claim 8 wherein the sidewalls comprise a dielectric material.

10. The apparatus of claim 1 wherein each scintillator has a tube shape and the scintillator array is configured in a fiber bundle having a protective sheath therearound.

11. The apparatus of claim 1 wherein the high frequency electromagnetic energy are x-rays and the x-rays are not converted to light energy before conversion to electrons.

12. A composite comprising a bulk and conducting material combination to convert high frequency electromagnetic energy directly to electrons and conduct the electrons to an electrical interconnect, wherein the bulk and conducting material are compacted and heat-treated in reduced atmosphere and are configured in a form selectable from one of a pixelated form, a columnated form, and a layered form having a plurality of conducting layers and a plurality of bulk layers.

13. The composite of claim 12 incorporated into a computed tomography system.

14. The composite of claim 12 incorporated into a radiation detector of a radiation emitting imaging apparatus comprising:
   an imaging bay;
   a table configured to position a subject to be imaged;
   a radiation projection source configured to project radiation toward the subject; and
   an image reconstructor configured to reconstruct an image of the subject from the electrons output by the radiation detector.

15. The composite of claim 12 wherein the conducting material converts the high frequency electromagnetic energy directly to electrons and conducts the electrons.

16. The composite of claim 12 wherein the bulk is selected from a group of materials consisting of undoped CsI, CsBr, and PbO.

17. The composite of claim 12 wherein the conducting material is selected from a group consisting of KCsSb, $Cs_3Sb$, RbCsSb, NaCsSb, and LiCsSb.

18. The composite of claim 12 wherein the conducting material is a semiconductor compound selected from a group consisting of CdTe, GaAs, InAs, GaAs—Cs, and PbTe.

19. The composite of claim 12 wherein each conducting layer has a width of approximately 5–15 micrometers and each bulk layer has a width of approximately 50–100 micrometers.

20. The composite of claim 12 wherein the bulk and conducting material are each powder.

21. A method for providing imaging electrons for a data acquisition system of a computed tomography system, comprising the steps of:

providing a scintillator capable of converting high frequency electromagnetic energy directly to electrons and conducting the electrons;

directing the high frequency electromagnetic energy toward a detector housing having therein the scintillator; and transmitting the electrons to a data processing system.

22. The method of claim 21 wherein the step of providing a scintillator includes compacting and sintering a mixture of bulk material capable of converting high frequency electromagnetic energy to electrons with conducting compound capable of conducting electrons and converting high frequency electromagnetic energy to electrons.

23. The method of claim 21 wherein the scintillator is formed of a bulk selected from a group of materials comprising undoped CsI, CsBr, and PbO, and a photoemissive conducting compound, wherein the photoemissive conducting compound is selected from a group consisting of KcsSb, $Cs_3Sb$, RbCsSb, NaCsSb, LiCsSb, CdTe, GaAs, InAs, GaAs—Cs, and PbTe.

24. The method of claim 21 including one of pixelating, columnating, and layering the scintillator into a scintillator array.

25. The method of claim 21 wherein the step of transmitting includes the step of providing at least one electrical interconnect forming a signal run extending from the scintillator to the data processing system.

26. The method of claim 21 wherein the high frequency electromagnetic energy are x-rays.

* * * * *